United States Patent [19]
Fischer et al.

[11] Patent Number: 5,464,348
[45] Date of Patent: Nov. 7, 1995

[54] SYRINGE SYSTEM FOR MATCHING TOOTH COMPOSITE COLORS

[75] Inventors: Dan E. Fischer, Sandy, Utah; Fred Picavet, Lancon de Province, France

[73] Assignee: Ultradent Products, Inc., South Jordan, Utah

[21] Appl. No.: 303,433

[22] Filed: Sep. 9, 1994

Related U.S. Application Data

[63] Continuation-in-part of Ser. No. 19,266, Feb. 16, 1993, Pat. No. 5,364,267.

[51] Int. Cl.⁶ .................................................. A61C 19/10
[52] U.S. Cl. ............................... 433/26; 433/90; 206/369
[58] Field of Search ................................. 433/89, 90, 26; 206/571, 63.5, 364, 368, 369

[56] References Cited

U.S. PATENT DOCUMENTS

| | | | |
|---|---|---|---|
| 4,492,576 | 1/1985 | Dragan | 433/90 |
| 4,657,138 | 4/1987 | Watson | 206/366 |
| 4,850,484 | 7/1989 | Denman | 206/366 |
| 5,083,921 | 1/1992 | Dragan | 433/90 |
| 5,199,567 | 4/1993 | Discko, Jr. | 206/369 |

OTHER PUBLICATIONS

Vita Lumen® Vacuum Shade Guide–Actual product sample on sale or in use in this country before Applicant's filing date.

Primary Examiner—Cary E. O'Connor
Attorney, Agent, or Firm—Workman Nydegger Seeley

[57] ABSTRACT

A syringe system for matching tooth composite colors to natural tooth colors. The system includes a plurality of delivery syringes each having therein a different colored tooth composite. In one embodiment, a visible portion of each delivery syringe is colored with the same color as the tooth composite within that delivery syringe. In another embodiment, an actual cured sample of the tooth composite contained within the syringe is placed on a visible portion of each delivery syringe. Therefore, matching tooth composite color to natural tooth color can be performed by simple viewing of the delivery syringes. An organizer displays the delivery syringes in such a way that the colored portion, or composite sample portion, of each delivery syringe is clearly visible. The organizer means also displays the delivery syringes in such way that the delivery syringes together provide a visible palette of colors from which to choose a matching tooth composite.

27 Claims, 11 Drawing Sheets

SYRINGE SYSTEM FOR MATCHING TOOTH COMPOSITE COLORS

RELATED APPLICATION INFORMATION

This application is a Continuation-in-part of United States application Ser. No. 08/019,266, filed Feb. 16, 1993, now U.S. Pat. No. 5,364,267, incorporated herein by reference.

BACKGROUND

1. Field of the Invention

The present invention relates to a system for matching tooth color to a tooth composite color. More particularly, the present invention relates to a system for displaying delivery syringes, each syringe having placed thereon an actual sample of the colored tooth composite contained within the syringe, in such a way that a palette of colors is provided by the display from which to match tooth color to the actual tooth composite colors contained within the delivery syringes.

2. Prior State of the Art

Cosmetic and/or functional augmentations of a tooth due to chipping or decay is a common dental procedure. Fortunately, it is a problem that dentists can easily solve. Typically, the dentist will apply a resin-based, light-activated tooth composite to the tooth in order to fill a chipped or missing area. When the tooth composite closely matches the natural color of the tooth, the repair job is barely, if at all, noticeable.

It is critical in this process, however, to accurately match the tooth composite color to the natural tooth. There are many shades of natural tooth colors. Without, care, it is possible for the dentist to accidentally apply the wrong tooth composite color.

At present, the method of choosing the matching color of tooth composite is unduly complex and time-consuming, and is subject to the risk of error.

Typically, a color display is used that comprises a rack of artificial or simulated teeth wherein each tooth is a different color. Each artificial tooth in the display is labeled with a code number which identifies the tooth composite color represented by the artificial tooth. The same code number is present on a delivery syringe containing that particular composite color. Once the correct color is decided upon, the user must then note the code number on the artificial tooth, and then retrieve the delivery syringe having thereon the same code number.

One problem with this method is that the codes are often small and difficult to see. As a consequence, the codes on either the colored artificial tooth or the corresponding delivery syringe may be misread, thereby resulting in the wrong choice of syringe. Thus, even if the natural tooth color is accurately matched, misreading of the code numbers can frustrate the job.

Therefore, the process of choosing a correct tooth composite can be time-consuming and must be performed with extra care. As a dentist's time is often in short supply, the extra time necessary for carefully reading the codes on the colored objects and matching those codes with the correct codes on the syringes, and then repeating the process when the codes have been misread, can often be frustrating and burdensome.

Additionally, misplacement or loss of any of the simulated tooth color samples or delivery syringes may further hamper and frustrate the job. It is also often difficult to quickly glance at an assortment of color samples and/or delivery syringes and to easily verify from the code numbers whether duplications and/or omissions of certain colors are present.

BRIEF SUMMARY AND OBJECTS OF THE INVENTION

The present invention seeks to resolve the above and other problems which have been experienced in the art. More particularly, the syringe system of this invention constitutes an important advancement in the art of matching natural tooth colors and using tooth composites, as evidenced by the following objects and advantages realized by the invention over the prior art.

One object of the present invention is to provide a syringe system for conveniently and efficiently matching tooth composite colors to natural tooth colors and obtaining the correct tooth composite in one simple step, without the need of simulated or artificial teeth or other objects.

Another object of the present invention is to provide a system for displaying delivery syringes having different tooth composite colors therein, whereby the color of the tooth composite can be chosen by simply looking at the color of the syringe, thereby eliminating any reference to code numbers and the like.

An additional object of the present invention is to provide a delivery syringe which can be used with a plurality of other similar delivery syringes so as to provide a palette of colors from which to match a patient's tooth color, wherein the color of the tooth composite contained within the syringe matches the color of the syringe, or a portion thereof.

Yet another object of the present invention is to provide a delivery syringe which can be used with a plurality of other similar delivery syringes so as to provide a palette of colors from which to match a patient's tooth color, wherein a sample of the tooth composite contained within the syringe is placed at a conspicuous portion on the exterior of the syringe, so as to allow easy and accurate comparison of the composite's color with the patient's tooth color.

Additional objects and advantages of the invention will be set forth in the description which follows, and in part will be obvious from the description, or may be learned by the practice of the invention. The objects and advantages of the invention may be realized and obtained by means of the instruments and combinations particularly pointed out in the appended claims.

To achieve the foregoing objects, and in accordance with the invention as embodied and broadly described herein, a syringe system is provided for conveniently and efficiently matching the color of a tooth composite to the natural color of a tooth to be repaired.

The syringe system comprises a plurality of delivery syringes, each delivery syringe containing therein a different colored tooth composite, and each delivery syringe being colored so as to match the color of the tooth composite contained therein. The plurality of delivery syringes together provides a palette of colors from which to match a patient's natural tooth color.

Each delivery syringe comprises at least a syringe barrel, a plunger, and a removable cap. The syringe barrel contains therein a tooth composite. Because the tooth composite can be light activated, the syringe barrel must be constructed of an opaque material to prevent light from entering the barrel.

The plunger is sized so as to be able to fit within the syringe barrel and slide longitudinally therein. The plunger is inserted into the syringe barrel and is used to push and extrude the tooth composite material from the syringe barrel.

The removable cap is used to enclose the end of the syringe barrel until such time as the tooth composite is to be extruded from the syringe barrel.

According to one embodiment of the present invention, the syringes, either the entire syringe or a portion thereof, are colored so as to match the color of the tooth composite contained therein. Therefore, the color of the tooth composite can easily be visually perceived simply by looking at the color of the syringe.

In another embodiment of the present invention, an actual cured sample of the same composite material contained within a delivery syringe is placed on a conspicuous portion of the syringe. This embodiment provides even further color matching accuracy because it can be insured that the actual color of the cured tooth composite matches the patient's tooth color, and which also assures accuracy due to shade changes of different lots of the composite material. As with the previous embodiment, the color of the composite contained within the syringe can be visually perceived simply by looking at the color of the sample composite portion, Preferably, the composite sample is positioned on an exterior portion of the delivery syringe so that it can be seen when the syringe is placed in the organizing means, and in a manner such that the composite sample can be easily compared with a patient's teeth.

An organizing means displays the delivery syringes in such a way that the syringes are prominently visible and accessible for use. The organizing means also displays the syringes in such way that a palette of colors is provided from which to match a patient's natural tooth color.

BRIEF DESCRIPTION OF THE DRAWINGS

In order to more completely understand the manner in which the above-recited and other advantages and objects of the invention are obtained, a more particular description of the invention briefly described above will be rendered by reference to specific embodiments thereof which are illustrated in the appended drawings. Understanding that these drawings depict only presently preferred embodiments of the invention and are therefore not to be considered limiting of its scope, the invention in its presently understood best mode for making and using the same will be described with additional specificity and detail through the use of the accompanying drawings in which.

DETAILED DESCRIPTION OF THE PREFERRED EMBODIMENTS

Figure 1:
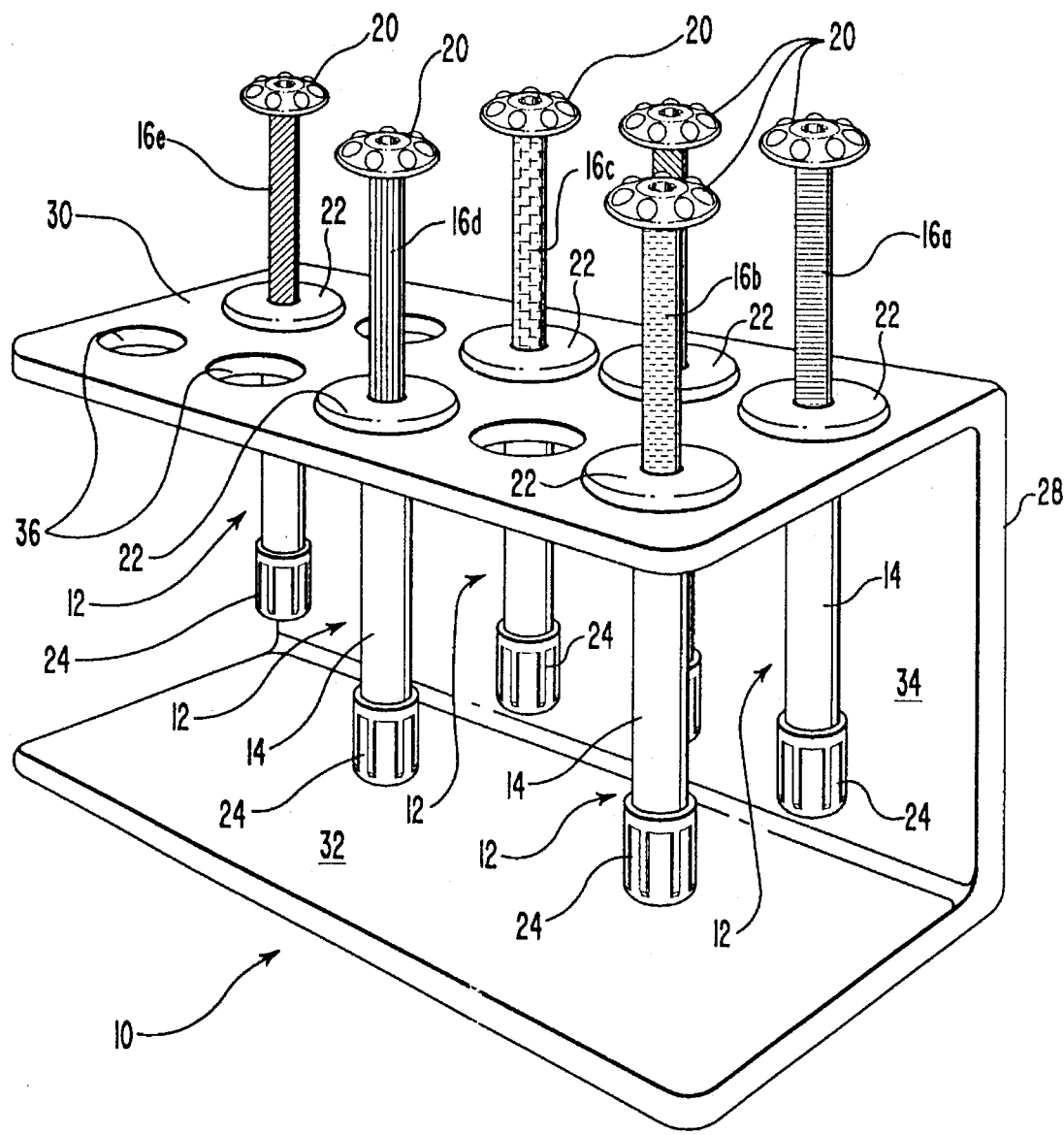
FIG. 1 is a perspective view of one preferred embodiment of the syringe system within the scope of the present invention wherein the plunger of each delivery syringe is colored.

Reference is now made to the drawings wherein like parts are designated with like numerals throughout. Referring first to FIG. 1, one presently preferred embodiment of the syringe system of the present invention is illustrated and generally designated at 10.

Syringe System 10 comprises a system for conveniently and efficiently matching tooth composite colors to natural tooth colors. The system comprises a plurality of delivery syringes 12 which each contain therein a different colored tooth composite. Each delivery syringe 12 is colored, in entirety or in part, so as to provide an indicia means for displaying the color of the tooth composite contained in the barrel of the delivery syringe so the color of the tooth composite can be easily matched to the color of the tooth. The plurality of delivery syringes 12 together provides a palette of colors from which to match a patient's natural tooth color.

Each syringe 12 comprises a syringe barrel 14. Syringe barrel 14 is generally cylindrical in shape and is adapted for holding a quantity of a dental composite material. As the material contained therein may be light activated, the syringe barrel 14 is constructed of an opaque material to prevent the passage of light.

Longitudinally slidable within syringe barrel 14 is a plunger 16. An enlarged head 20 is located at the proximal end of the plunger 16. Plunger 16 is slidably contiguous with the inner wall of the syringe barrel 14. In addition, plunger 16 is preferably constructed of a material which is non-reactive with the tooth composite.

At the proximal end of syringe barrel 14 is a circular disk 22. Although conventional syringes function by placing two fingers on the disk 22 and depressing the enlarged head 20 with the thumb, the syringe 12 may also be used by placing the fingers and thumb around the syringe barrel 14 and depressing enlarged head 20 by the palm of the hand.

A removable opaque cap 24 is selectively attachable to the distal end of syringe barrel 14. Removable cap 24 is used for enclosing the end of syringe barrel 14 until such time as the tooth composite is to be extruded from the barrel 14.

As earlier stated, at least one of the parts of each delivery syringe 12 is comprised of an indicia means, as for example a colored portion that matches the color of the tooth composite contained in syringe barrel 14. The color of the tooth composite in each delivery syringe 12 can be thereby visually perceived simply by looking at the colored portion of each delivery syringe 12.

Figure 2:
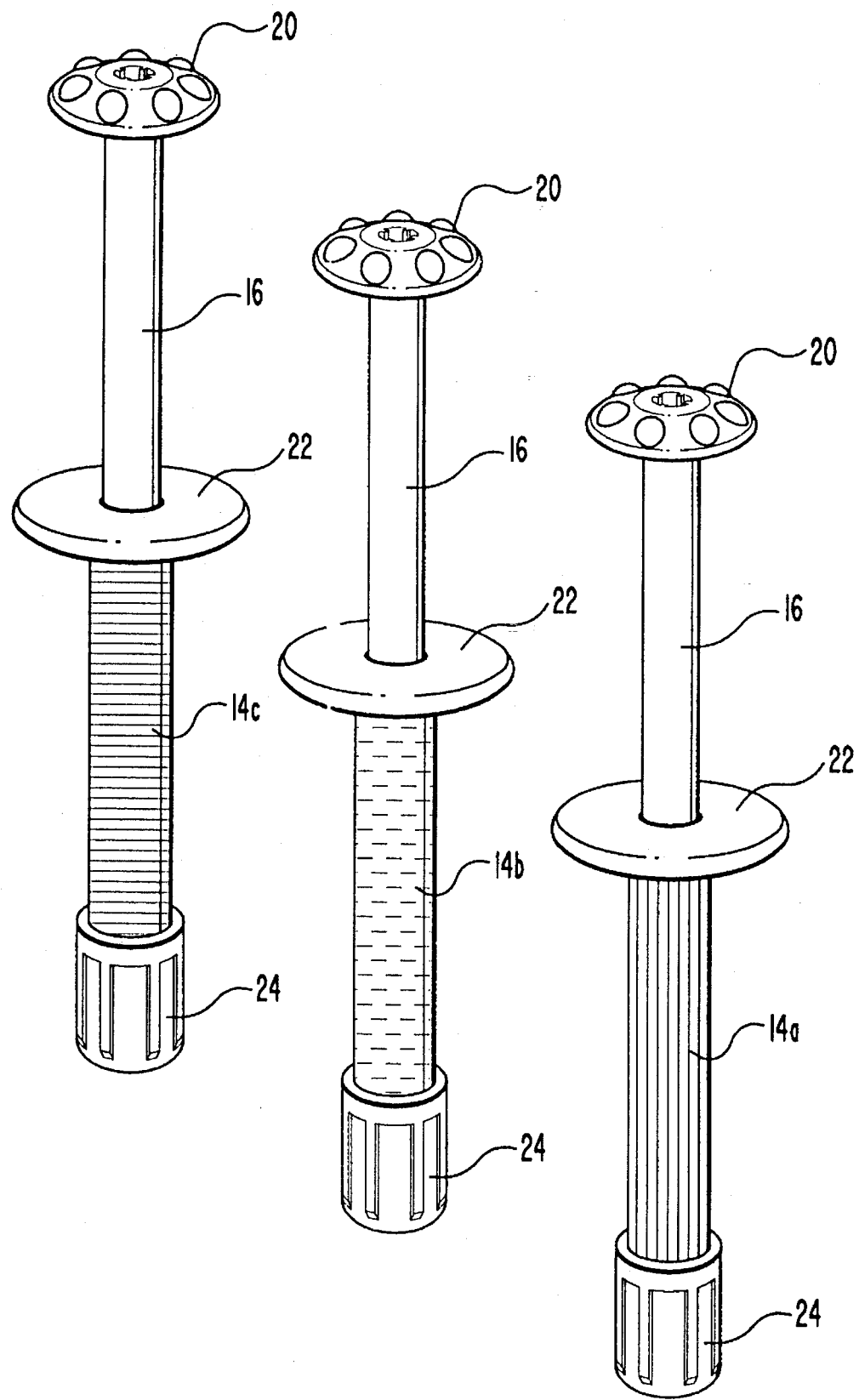
FIG. 2 schematically illustrates another embodiment of the syringe system wherein the entire barrel of each syringe is marked with a color which indicates the color of the tooth composite contained therein.

Various parts of each delivery syringe may be colored. For example, as shown in FIG. 1, the plunger 16a–16e of each delivery syringe 12 may be colored so as to match the color of the tooth composite contained in each particular syringe. As shown in FIG. 2, the entire syringe barrel 14 may be colored. In FIG. 2, three delivery syringes 12 are shown each having a different colored barrel 14a–14c corresponding to the color of the tooth composite within each barrel. When placed together, the syringes provide a palette of colors from which to select a color matching a natural tooth color.

Small portions of each syringe part, as opposed to the entire part, may also be colored. For example, the syringe barrel 14 may be striped with a color which matches the color of the tooth composite contained in that barrel. Further, the finger disks 22 rather than the entire barrel 14, or the enlarged head 20 rather than the entire plunger 16, may be colored.

Figure 3:
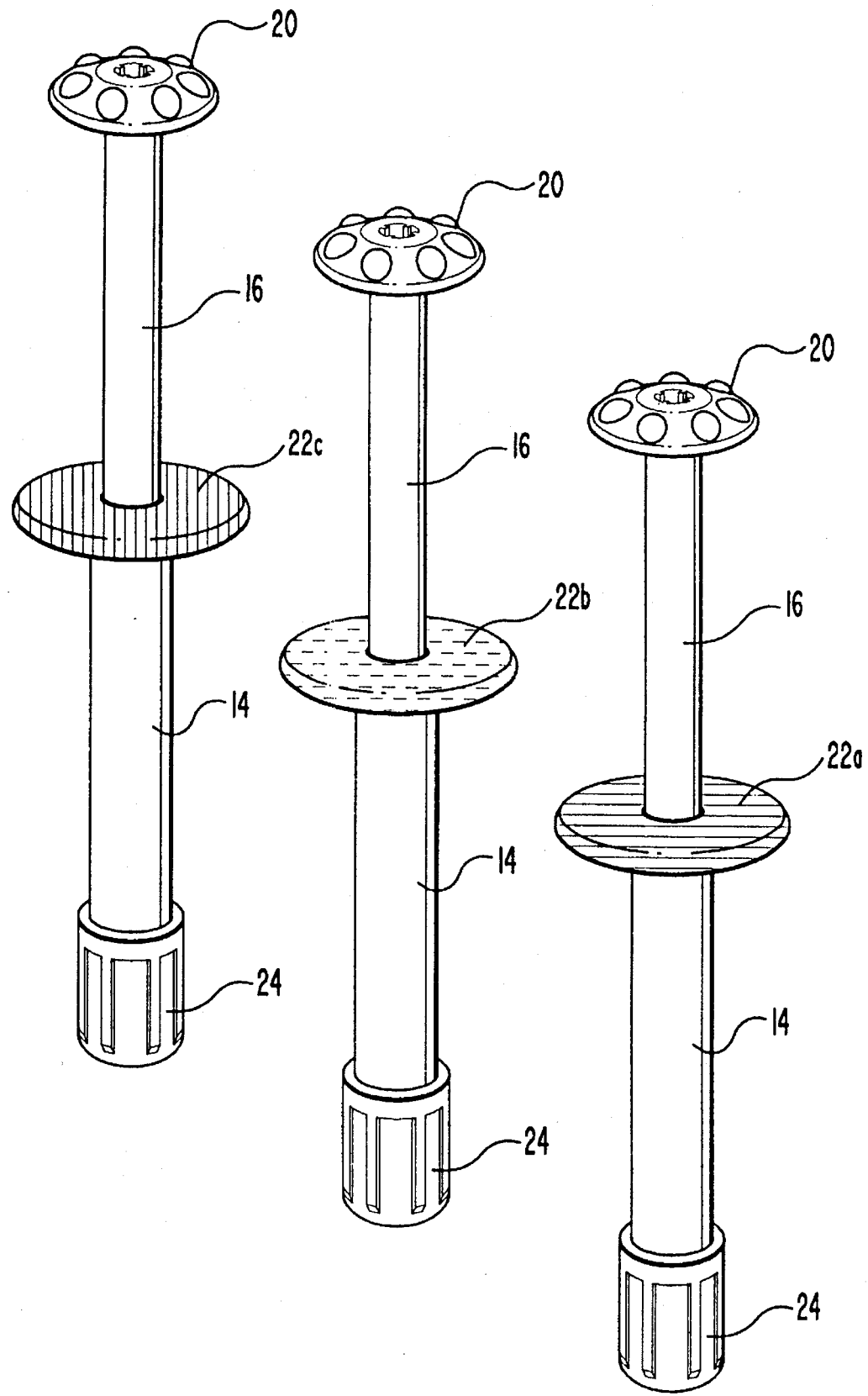
FIG. 3 schematically illustrates yet another embodiment of the syringe system wherein the disks of each syringe is marked with a color which indicates the color of the tooth composite contained within the syringe.
Figure 4:
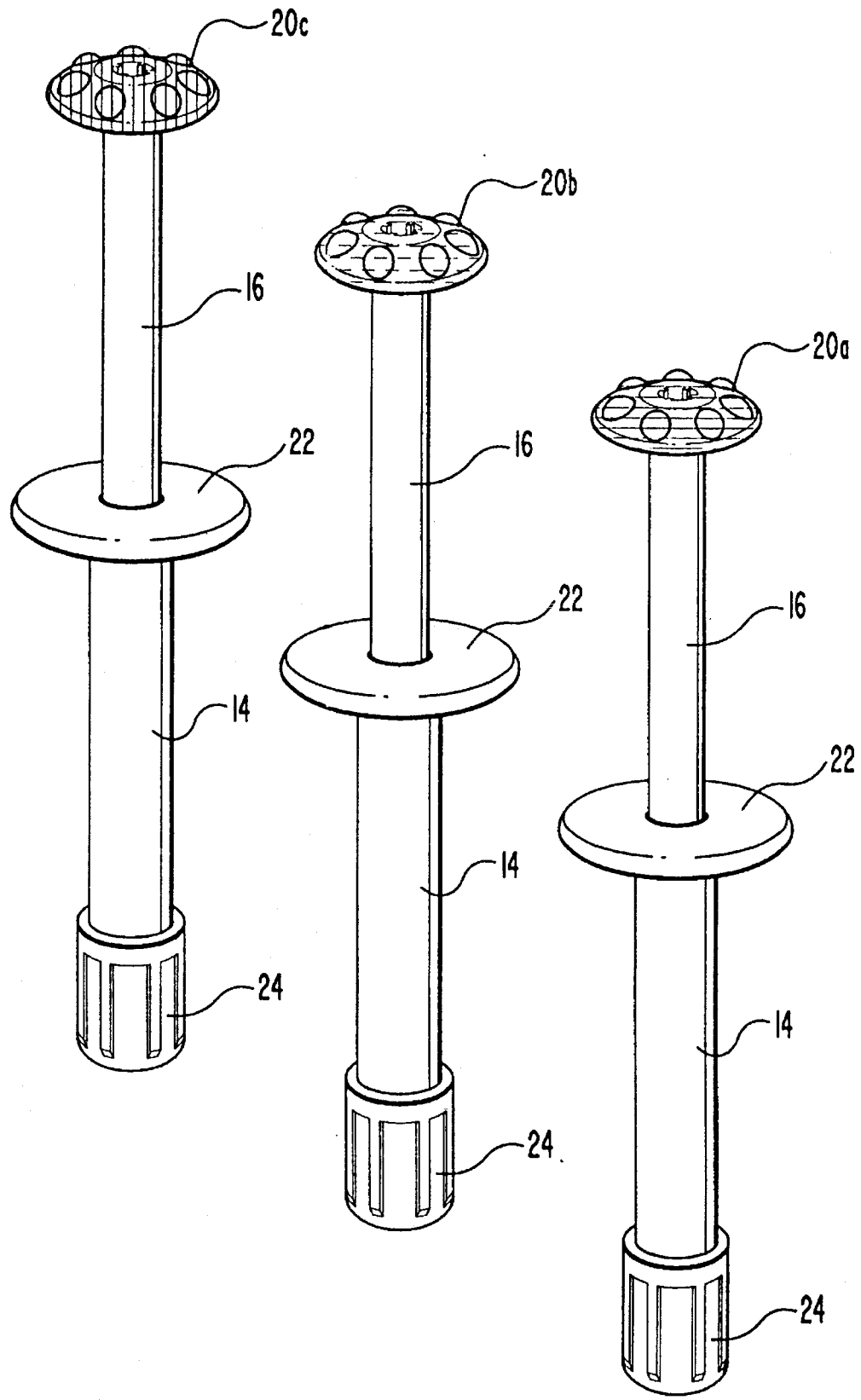
FIG. 4 schematically illustrates yet another embodiment of the syringe system wherein the enlarged head connected to the plunger of each syringe is marked with a color which indicates the color of the tooth composite contained within the syringe.
Figure 5:
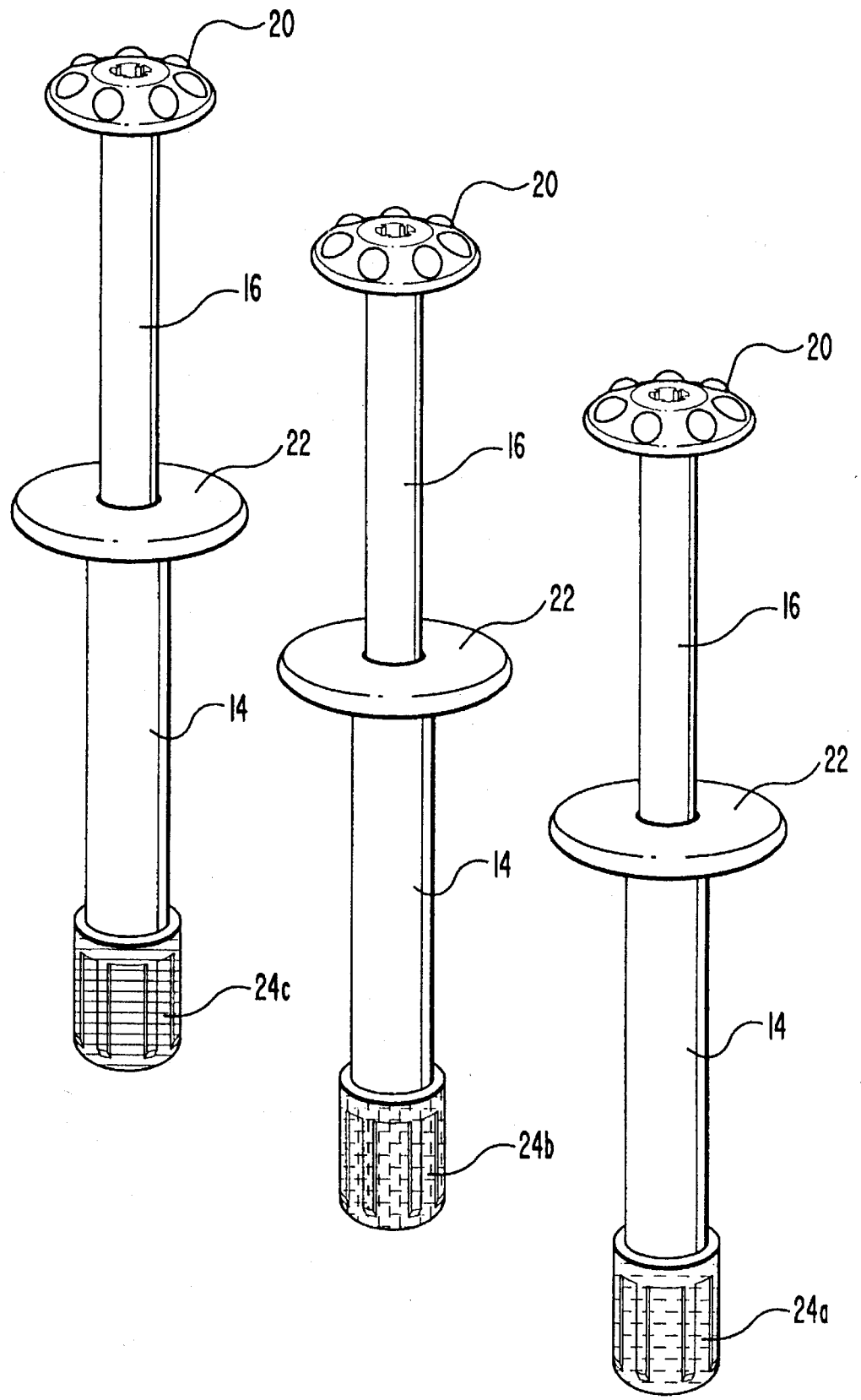
FIG. 5 schematically illustrates yet another embodiment of the syringe system wherein the removable cap of each syringe is marked with a color which indicates the color of the tooth composite contained within the syringe.
Figure 6:
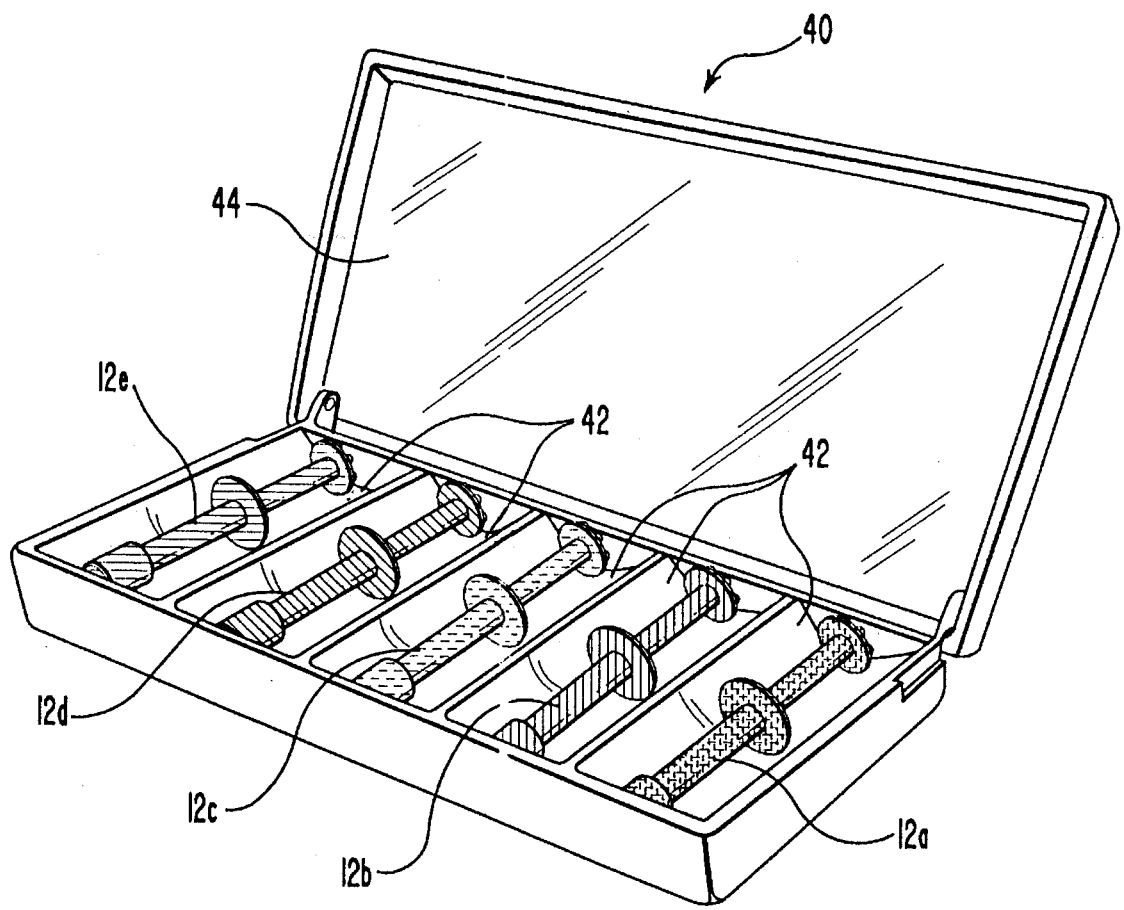
FIG. 6 illustrates an alternate embodiment of the organizing means of the present invention wherein the plurality of syringes are displayed in a transparent box.

In FIG. 3, the disks 22a–22c of three delivery syringes 12 are shown colored in different shades. In FIG. 4, the enlarged heads 20a–20c of each of three delivery syringes 12 is shown to be colored. In FIG. 5, the removable caps 24a–24c of each of three delivery syringes 12 is shown to be colored. In FIG. 6, each syringe 12a–12d is colored in its entirety. In each figure, a range of colors is provided by the different colored syringes.

It will be appreciated that the coloring of a wide variety of parts, and combinations of parts, is possible and within the scope of the present invention. In the preferred embodiment, however, the same part of each delivery syringe is colored. Thus, the delivery syringes can be laid or held side-by-side to display the possible range of colors.

The system of the present invention further comprises organizing means for displaying the plurality of delivery syringes in such a way that the colored portion on each delivery syringe 12 is prominently visible. With this organizing means, matching tooth composite color with natural tooth color is convenient and easy.

Referring back to FIG. 1, one preferred embodiment of the organizing means is illustrated. As illustrated in FIG. 1, the organizing means comprises an organizer 28 having an upper shelf 30 and a bottom support 32. A back wall 34 connects upper shelf 30 and a bottom support 32. Upper shelf 30 is comprised of a plurality of openings 36. Each opening 36 is sized so as to easily allow passage of the syringe barrel 14 of each delivery syringe 12, but prohibit passage of the disk 22. When each delivery syringe 12 is inserted downward into one of the plurality of openings 36, the disk 22 of each delivery syringe 12 is barred from passage through the opening 36 so that each delivery syringe 12 is suspended between the upper shelf 30 and the bottom support 32. While suspended, the colored portion of each delivery syringe 12 can be easily viewed and is held side-by-side in relation to the other syringes 22.

An alternate embodiment of the organizing means of the present invention is illustrated in FIG. 6. A box 40 is shown divided into a plurality of compartments 42. Each compartment 42 is sized such that a delivery syringe 12 fits comfortably therein. A transparent cover 44 may be positioned over box 40 so that the palette of colors provided by the plurality of delivery syringes may be easily viewed, while preventing contamination of the syringes.

It can be appreciated that any organizing means which displays the plurality of delivery syringes 12 such that the colored portions of the delivery syringes are conspicuously visible is within the scope of the present invention.

Further, it is preferred that the organizing means display at least some of the delivery syringes in horizontal alignment so that the colored part of each delivery syringe is held immediately adjacent to the colored part of each adjacent delivery syringe. This provides the optimum view of the palette of colors provided by the display of delivery syringes. The alignment would emphasize the range of colors available from which to match the patient's teeth.

Figure 7:
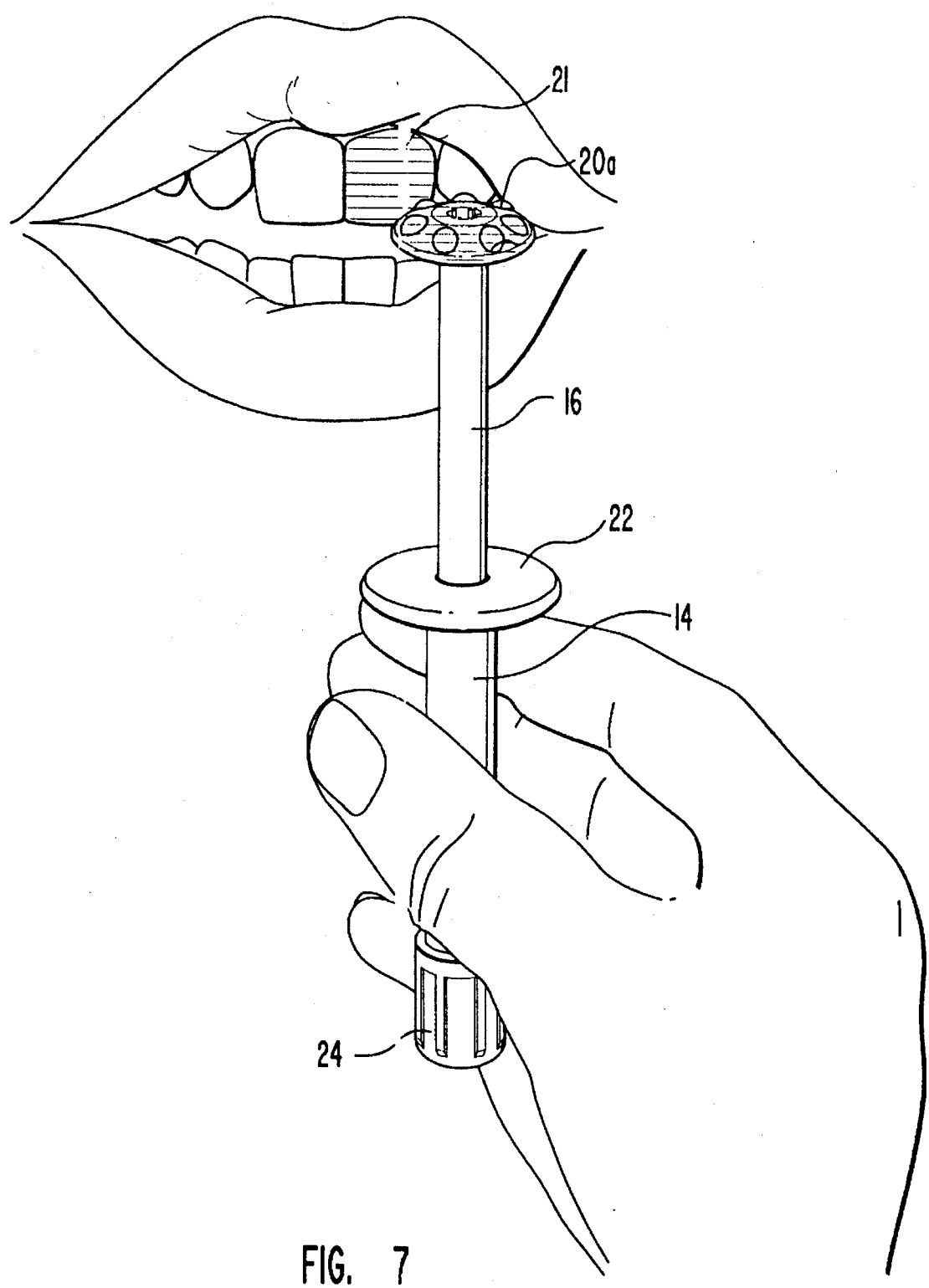
FIG. 7 illustrates a user of the present invention matching the color of a part of a syringe to the natural color of a patient's tooth.

With the system of the present invention, the procedure of matching tooth composite color to a natural tooth color and then obtaining the correct tooth composite color can be accomplished in one step. As illustrated in FIG. 7, each delivery syringe 12 that is selected can be held up to a tooth 21 so as to compare the colored portion 20a of the syringe 12 with the tooth 21. If the color is not matched, another syringe 12 may be compared. If the color is matched, then the syringe 12 and its tooth composite can then be used to perform the required cosmetic or functional augmentation on the matched tooth.

The additional step in the prior art of having to obtain the correct syringe, after the color has first been determined through use of separate comparison objects, is eliminated. With the present invention, choosing the color and obtaining the correct syringe is performed in one step. Valuable time and energy is saved, and the possibility of mistakenly choosing the wrong syringe is virtually eliminated.

In yet another embodiment of the syringe system of the present invention, an indicia means for displaying the color of the tooth composite contained within the delivery syringe 12, is placed on an exterior portion of each delivery syringe 12. This indicia means is formed from a cured sample of the same tooth composite material that is contained within the particular delivery syringe 12. Thus, the color of the sample portion is identical to the color of the tooth composite contained within a delivery syringe 12, and a user can easily identify and select the correct delivery syringe 12. As in the previous embodiment, the procedure of matching a syringe containing a particular tooth composite color to a natural tooth color is accomplished in one step. Further, because the user can compare the tooth color to an actual cured sample of composite material, selection can be based not only on similarities of color, but on similarities of texture, shading, brightness or other characteristics that may not be possible when comparison is based only upon a colored copy of the composite. Thus, a closer match may potentially be obtained.

Figure 8:
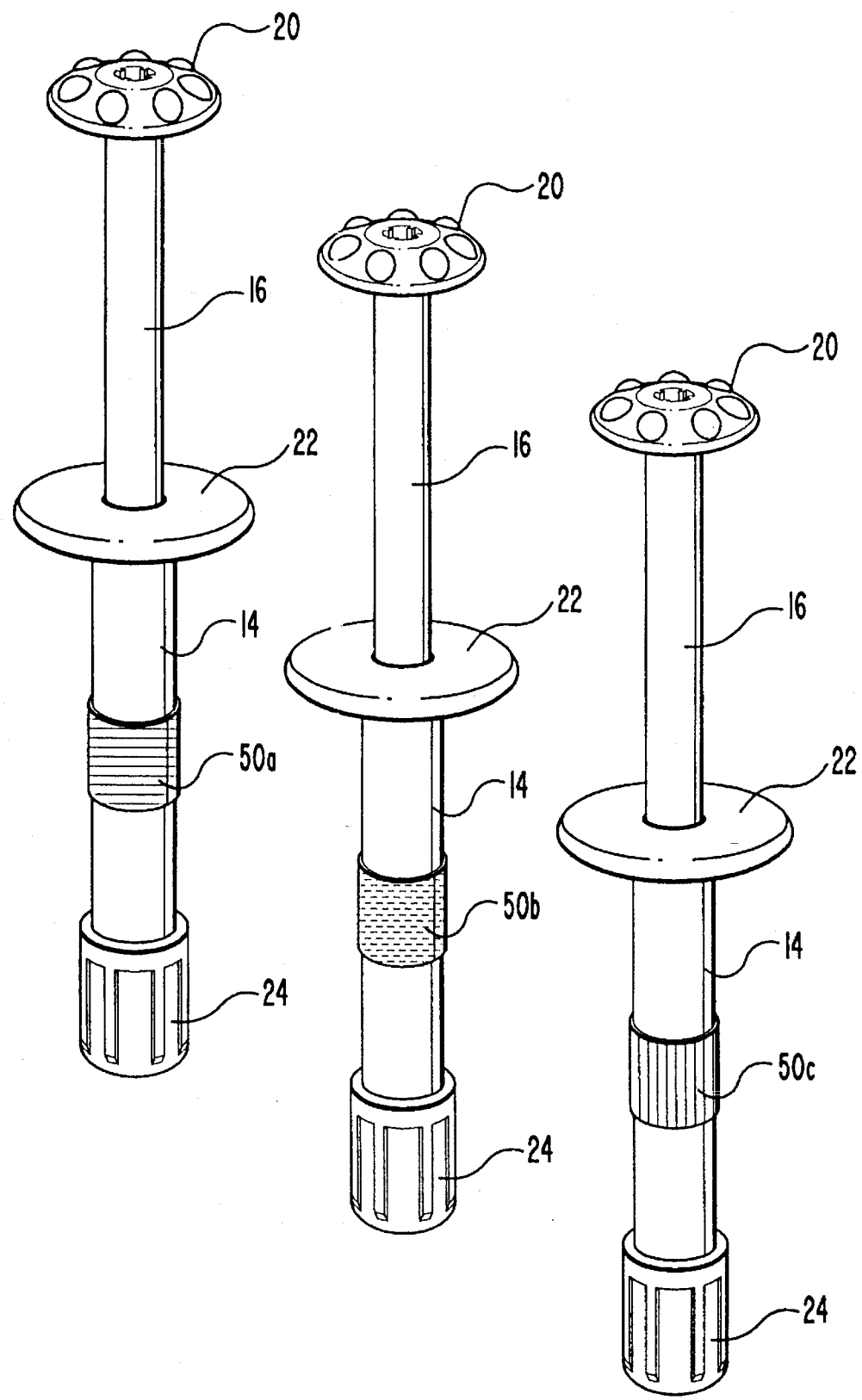
FIG. 8 schematically illustrates yet another embodiment of the syringe system wherein a cured sample of the composite contained within the syringe is visibly placed on the syringe barrel.

The indicia means, which is comprised of a sample portion of tooth composite, may be implemented in variety of ways and may be placed on various parts of the delivery syringe 12, and still be within the intended scope of the present invention. For example, as shown in FIG. 8, the indicia means comprises a band 50a–50c that is formed around the circumference of the barrel 14 of each delivery syringe 12. Again, each band 50a–50c is made from the same composite material contained within the particular delivery syringe, and thus will have a color that matches exactly the color of the tooth composite contained in the syringe.

Figure 9:
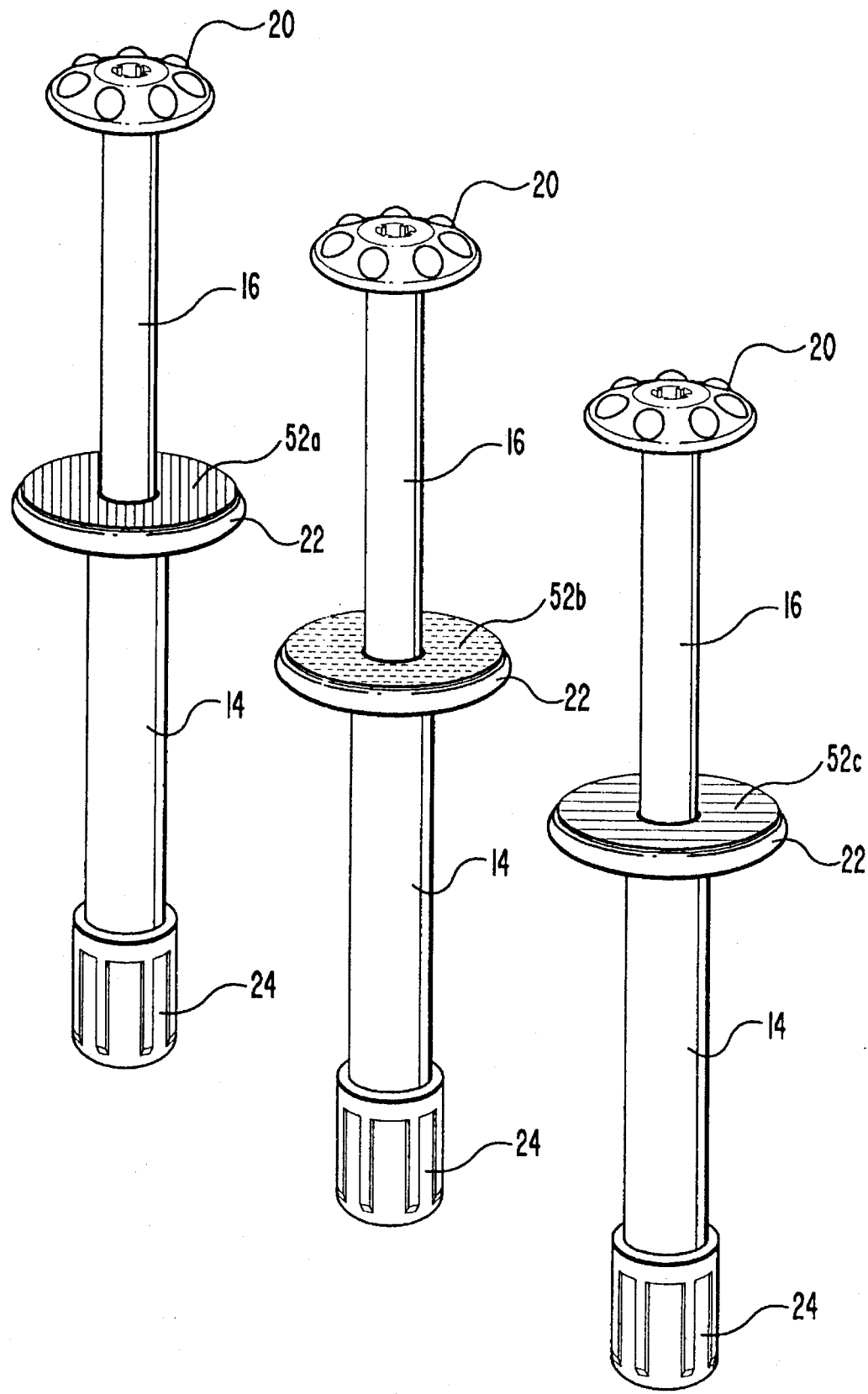
FIG. 9 schematically illustrates yet another embodiment of the syringe system wherein a cured sample of the composite contained within the syringe is visibly placed on the disk portion of each syringe.
Figure 10:
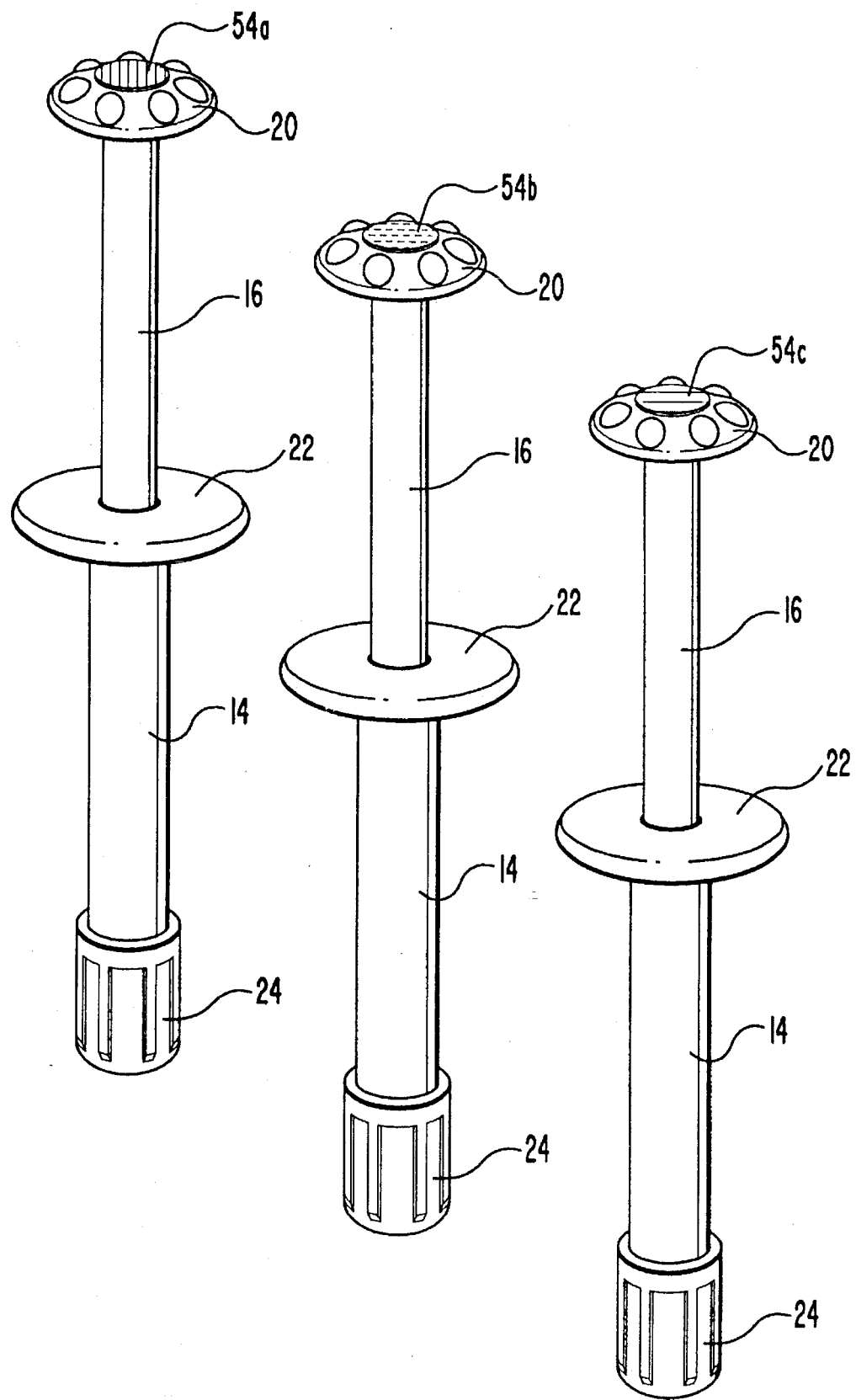
FIG. 10 schematically illustrates yet another embodiment of the syringe system wherein a cured sample of the composite contained within the syringe is visibly placed on the enlarged head portion that is connected to the plunger of each syringe.
Figure 11:
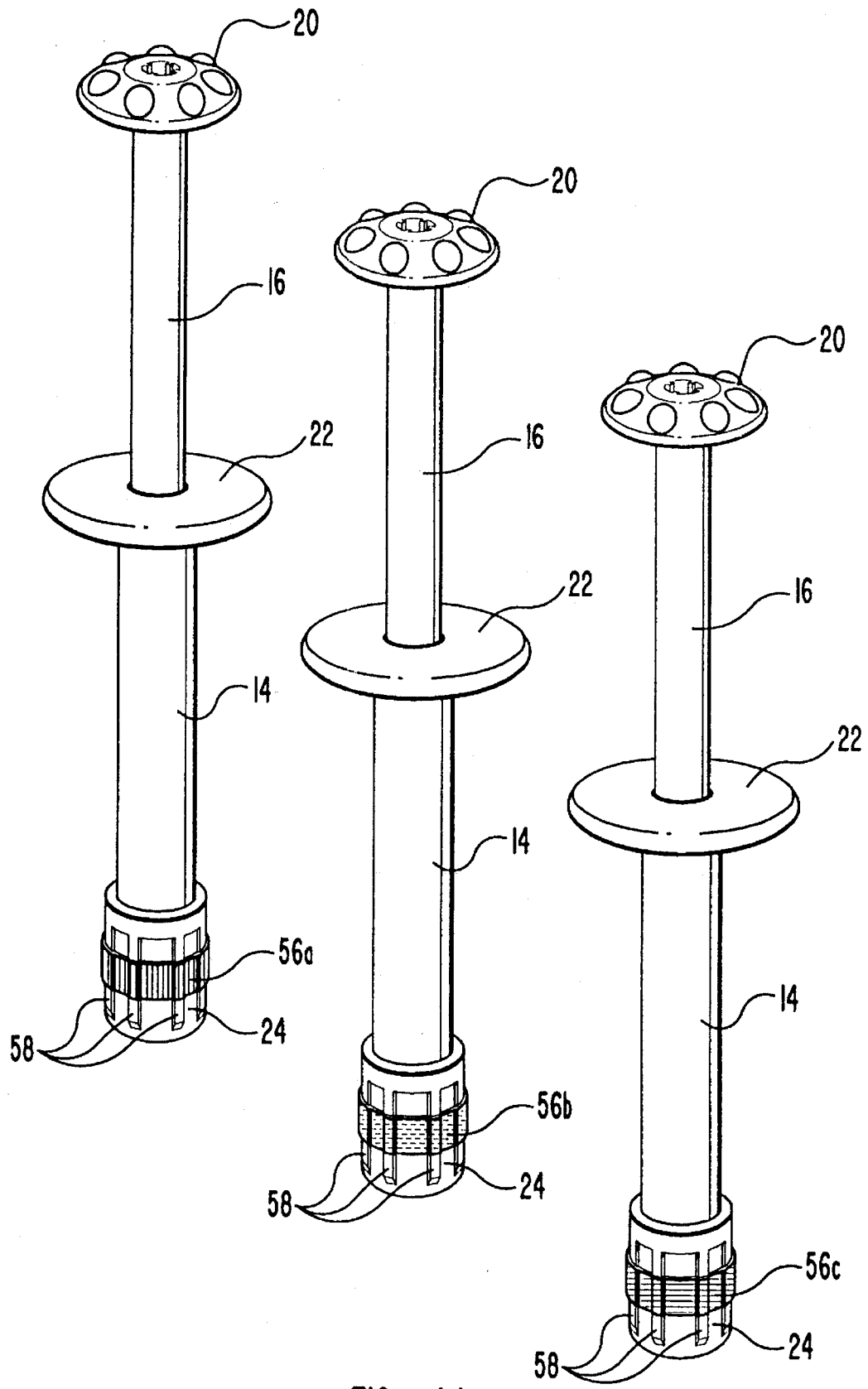
FIG. 11 schematically illustrates yet another embodiment of the syringe system wherein a cured sample of the composite contained within the syringe is visibly placed on the removable cap of each syringe.

FIG. 9 exemplifies another manner in which the indicia means can be implemented. As is shown, the indicia means is comprised of an overlay 52a–52c that is formed on the upper surface of each finger disk 22. As is shown in FIG. 10, the indicia means can also be implemented, for example, by placing the sample composite into a recess 54a–54c that is formed at the center of each enlarged plunger head 20. Alternatively, FIG. 11 illustrates the indicia means as being comprised of a band 56a–56c that is formed around the removable cap 24 of each delivery syringe 12. Instead of forming a band around the cap 24, the indicia means could also be implemented by placing composite material between the ridges 58 that are disposed on each cap 24.

As generally discussed, in each of these embodiments the indicia means is comprised of a sample portion of the same composite material that is contained within the particular delivery syringe 12. Thus, the sample portions of composite that make up the indicia means-can be prefabricated, and then later affixed with a suitable adhesive to the corresponding syringe part. Alternatively, the delivery syringe 12, or parts of the delivery syringe, can be manufactured so as to have the portion of sample composite placed thereon. Further, the composite sample could be applied to preexisting delivery syringes 12. For example, the recess 54 discussed above in connection with FIG. 10 could be filled with a particular composite and, after the composite has hardened, the syringe would be color coded for that particular composite.

As with the previous embodiment, when placed together, the syringes provide, by way of the indicia means, a palette of colors from which to select a color matching a natural tooth color. It can be appreciated that the coloring of a wide variety of syringe parts, and combinations of syringe parts, based on the positioning of the sample composite material, is possible and within the scope of the present invention. In the preferred embodiment, however, the sample composite material is placed on the same part of each delivery syringe 12 within a syringe system 10. Thus, the delivery syringes can be laid or held side-by-side to display the possible range of colors.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Patent is:

1. A syringe system for conveniently and efficiently matching tooth composite colors to natural tooth colors comprising:
   a) a plurality of delivery syringes, each delivery syringe containing therein a different colored tooth composite, and each said delivery syringe comprising at least the following parts:
      a barrel in which the tooth composite is contained and which is constructed of an opaque material to prevent light activation of the tooth composite;
      a plunger longitudinally slidable within the barrel for extruding the tooth composite from the barrel; and
      a removable cap for enclosing the end of the barrel until such time as the tooth composite is to be extruded from the barrel; and
   b) indicia means, placed on at least one of said parts of each delivery syringe, for displaying the color of the tooth composite contained in the barrel of the delivery syringe, the indicia means comprising:
      a cured sample of the composite contained within the delivery syringe barrel;
      whereby the indicia means is colored so as to match the color of the tooth composite contained in the barrel.

2. A system as defined in claim 1, wherein the syringe system further comprises organizing means for displaying the plurality of delivery syringes such that each delivery syringe is prominently visible.

3. A system as defined in claim 1, wherein the indicia means is placed on at least a portion of the barrel.

4. A system as defined in claim 1, wherein the indicia means is placed on at least a portion of the plunger.

5. A system as defined in claim 1, wherein the indicia means is placed on at least a portion of the removable cap.

6. A system as defined in claim 1, wherein the parts of the delivery syringe further comprise a disk outwardly protruding from the barrel.

7. A system as defined in claim 6, wherein the indicia means is placed on at least a portion of the disk.

8. A system as defined in claim 1, wherein the parts of the delivery syringe further comprises an enlarged head connected to the plunger for use in pushing the plunger into the barrel.

9. A system as defined in claim 8, wherein the indicia means is placed on at least a portion of the enlarged head.

10. A system as defined in claim 9, wherein the enlarged head has a recess formed therein, and the indicia means is disposed within the recess.

11. A system as defined in claim 1, wherein the organizing means is configured such that at least some of the plurality of delivery syringes are displayed in horizontal alignment such that the indicia means of each delivery syringe is held immediately adjacent to the indicia means of each adjacent delivery syringe.

12. A system as defined in claim 11, wherein the organizing means comprises a lower support and an upper display shelf, said upper shelf being comprised of a plurality of openings, each opening being sized so as to easily allow passage of the barrel of each delivery syringe, but prohibit passage of the disk, such that when each delivery syringe is inserted downward into one of the plurality of openings, the disk of each delivery syringe is barred from passage through the opening so that each delivery syringe is suspended between said upper shelf and said lower support.

13. A system as defined in claim 11, wherein the organizing means comprises a box having therein a plurality of compartments positioned side-by-side, each compartment having a width and length so as to accommodate the width and length of each delivery syringe, and each compartment prominently displaying each delivery syringe such that the indicia means of each delivery syringe is visibly conspicuous.

14. A syringe system for conveniently and efficiently matching tooth composite colors to natural tooth colors comprising:
   a) a plurality of delivery syringes, each delivery syringe containing therein a different colored tooth composite, and each said delivery syringe comprising at least the following parts:
      a barrel in which the tooth composite is contained and which is constructed of an opaque material to prevent light activation of the tooth composite;

a plunger longitudinally slidable within the barrel for extruding the tooth composite from the barrel; and a removable cap for enclosing the end of the barrel until such time as the tooth composite is to be extruded from the barrel;

b) indicia means, placed on at least one of said parts of each delivery syringe, for displaying the color of the tooth composite contained in the barrel of the delivery syringe, the indicia means comprising:

a cured sample of the composite contained within the delivery syringe barrel;

whereby the indicia means is colored so as to match the color of the tooth composite contained in the barrel; and (c) organizing means for displaying the plurality of delivery syringes in a manner such that the indicia means of each delivery syringe is prominently visible and whereby the color of the tooth composite in each syringe can be visually perceived simply by looking at the indicia means of each delivery syringe, the plurality of delivery syringes together providing a palette of colors from which to match a patient's tooth color.

15. A system as defined in claim 14, wherein the indicia means is placed on at least a portion of the barrel.

16. A system as defined in claim 14, wherein the indicia means is placed on at least a portion of the plunger.

17. A system as defined in claim 14, wherein the indicia means is placed on at least a portion of the removable cap.

18. A system as defined in claim 14, wherein the parts of the delivery syringe further comprise a disk outwardly protruding from the barrel.

19. A system as defined in claim 18, wherein the indicia means is placed on at least a portion of the disk.

20. A system as defined in claim 14, wherein the parts of the delivery syringe further comprises an enlarged head connected to the plunger for use in pushing the plunger into the barrel.

21. A system as defined in claim 20, wherein the indicia means is placed on at least a portion of the enlarged head.

22. A system as defined in claims 15, 16, 17, 19, or 21, wherein the organizing means is configured such that at least some of the plurality of delivery syringes are displayed in horizontal alignment such that the indicia means of each delivery syringe is held immediately adjacent to the indicia means of each adjacent delivery syringe.

23. A system as defined in claim 22, wherein the organizing means comprises a lower support and an upper display shelf, said upper shelf being comprised of a plurality of openings, each opening being sized so as to easily allow passage of the barrel of each delivery syringe, but prohibit passage of the disk, such that when each delivery syringe is inserted downward into one of the plurality of openings, the disk of each delivery syringe is barred from passage through the opening so that each delivery syringe is suspended between said upper shelf and said lower support.

24. A system as defined in claim 22, wherein the organizing means comprises a box having therein a plurality of compartments positioned side-by-side, each compartment having a width and length so as to accommodate the width and length of each delivery syringe, and each compartment prominently displaying each delivery syringe such that the indicia means of each delivery syringe is visibly conspicuous.

25. A system as defined in claim 20, wherein the enlarged head has a recess formed therein, and the indicia means is disposed within the recess.

26. A syringe system for conveniently and efficiently matching tooth composite colors to natural tooth colors comprising:

a) a plurality of delivery syringes, each delivery syringe containing therein a different colored tooth composite, and each said delivery syringe comprising at least the following parts:

a barrel in which the tooth composite is contained and which is constructed of an opaque material to prevent light activation of the tooth composite;

a plunger longitudinally slidable within the barrel for extruding the tooth composite from the barrel; and a removable cap for enclosing the end of the barrel until such time as the tooth composite is to be extruded from the barrel;

b) a cured sample of tooth composite placed on at least one of said parts of each delivery syringe, the cured sample being comprised of the same type of composite that is contained within the delivery syringe barrel, whereby the color of the cured sample of tooth composite matches the color of the tooth composite contained in the barrel;

(c) organizing means for displaying the plurality of delivery syringes in a manner such that the sample portion on each delivery syringe is prominently visible and whereby the color of the tooth composite in each syringe can be visually perceived simply by looking at the sample portion on each delivery syringe, the plurality of delivery syringes together providing a palette of colors from which to match a patient's tooth color.

27. A system as defined in claim 26, wherein the sample portion is placed on the same part of each of the delivery syringes contained within the syringe system.

* * * * *

UNITED STATES PATENT AND TRADEMARK OFFICE
CERTIFICATE OF CORRECTION

PATENT NO. : 5,464,348

DATED : November 7, 1995

INVENTOR(S) : DAN E. FISCHER, et al.

It is certified that error appears in the above-identified patent and that said Letters Patent is hereby corrected as shown below:

Col. 8, line 26, "comprises" should be --comprise--

Col. 9, line 35, "comprises" should be --comprise--

Col. 3, line 22, "portion," should be --portion.--

Col. 3, line 58, "is" should be --are--

Col. 5, line 20, "provide-a" should be --provide a--

Col. 5, line 33, "is shown" should be --are shown--

Col. 7, line 20, "means-can" should be --means can--

Signed and Sealed this

Twenty-second Day of April, 1997

BRUCE LEHMAN

*Commissioner of Patents and Trademarks*

*Attest:*

*Attesting Officer*